US00PP17546P2

(12) United States Plant Patent
Kordes

(10) Patent No.: US PP17,546 P2
(45) Date of Patent: Apr. 3, 2007

(54) FLORIBUNDA ROSE PLANT NAMED: 'KORAMASTI'

(50) Latin Name: *Rosa hybrida*
Varietal Denomination: Koramasti

(75) Inventor: Tim-Hermann Kordes, Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 40 days.

(21) Appl. No.: 11/133,754

(22) Filed: May 20, 2005

(51) Int. Cl.
*A01H 5/00* (2006.01)

(52) U.S. Cl. ..... Plt./151

(58) Field of Classification Search ..... Plt./151, Plt./150, 139, 140
See application file for complete search history.

(56) References Cited

FOREIGN PATENT DOCUMENTS

QZ 2004/1032 6/2004

*Primary Examiner*—Kent Bell
*Assistant Examiner*—June Hwu

(57) ABSTRACT

A new and distinct variety of Floribunda rose plant which has attractive red colored flowers and attractive green and glossy foliage. The buds are pointed and well turbinated. This new variety is having high production of long stems with a long vase life, vigorous, upright growth, and good tolerance to powdery mildew. The variety successfully propagates from softwood cuttings and is well suitable for year round production of cut flowers in commercial glass houses as a flowering cut rose. This and distinct variety has shown to be uniform and stable in the resulting generations from asexual propagation.

1 Drawing Sheet

Figures 1, 2, 3, 4, 5, 6, 7, 8, 9, 10, 11, 12, 13:
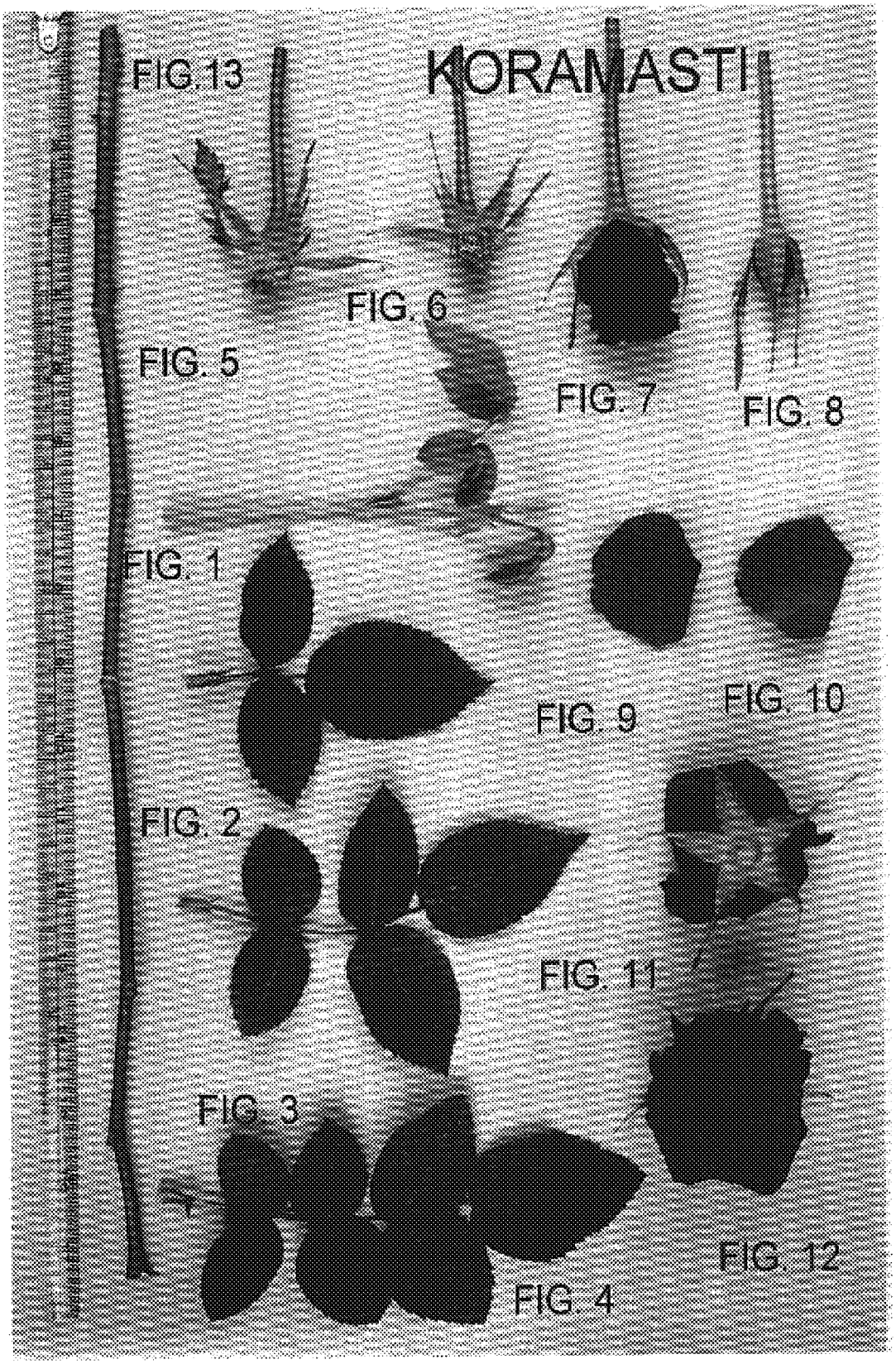

Latin name of genus and species: *Rosa hybrida* 'Koramasti'.

Variety denomination: The new variety is named 'Koramasti'.

BACKGROUND OF THE INVENTION

The present invention constitutes a new and distinct variety of floribunda rose plant, which was developed by artificially pollinating an unnamed seedling (not patent in the US) with an unnamed seedling (not patent in the US). The two parents were crossed in the summer of 1999 and the resulting seed was sown in December 1999, in a controlled glasshouse environment. Out of these seedlings one seedling was selected, as the new variety and named 'Koramasti'. The new rose may be distinguished from its seed parent, an unnamed seedling, by the following combination of characteristics:

1. 'Koramasti' has double flowers, while the unnamed seedling has medium single flowers.
2. 'Koramasti' has red colored petals, while the unnamed seedling has orange-red petals.

The new variety may distinguished from its pollen parent, an unnamed seedling created by the same inventor, by the following combination of characteristics:

1. 'Koramasti' has bigger flowers and foliage as compared to the unnamed seedling.
2. 'Koramasti' has red colored petals, while the unnamed seedling has light red colored petals.

BRIEF SUMMARY OF THE INVENTION

Initial asexual reproduction of 'Koramasti' by cuttings was first done in Klein Offenseth-Sparrieshoop, Germany.

The reproduction was conducted in controlled greenhouse environments.

Have here proven to be stable—by propagation with cuttings in several generations.

'Koramasti' is a high productive floribunda rose with a vase life of approximately 16 days.

'Koramasti' under conventional greenhouse production (18 degree Celsius nights, and 26 Celsius days) in Germany will produce 250–400 stems per year, averaging 45 cm long.

The objective of the hybridization of this rose variety for commercial greenhouse culture was to create a new and distinct variety with:

1. Uniform and abundant red flowers with good vase life.
2. Attractive long lasting foliage and strong growth.
3. Year round flowering under glasshouse conditions.
4. Suitability for production from softwood cuttings.
5. Durable flowers and foliage which make the variety suitable for distribution in the floral industry.

This combination of qualities was not present in previously available commercial cultivars of this type and distinguishes 'Koramasti' from all other varieties of which we are aware.

The seeds from hybridization were planted in a controlled environment and evaluations were conducted on the resulting plants. 'Koramasti' was selected by Tim-Herrmann Kordes in his development program in Klein Offenseth-Sparrieshoop, Germany.

BRIEF DESCRIPTIONS OF THE DRAWINGS

The accompanying color illustrations show as true as is reasonably to obtain in color photographs of this type, the typical characteristics of the buds, flowers, leaves, stems of 'Koramasti'. Specifically illustrated in:

Photo sheet:

FIG. 1. Young shoot.

FIG. 2. Three leaflets upper side.

FIG. 3. Five leaflets upper side.

FIG. 4. Seven leaflets upper side.

FIG. 5. Receptacle showing pistils (stamens removed).

FIG. 6. Receptacle showing stamens and pistils.

FIG. 7. Bud at the opening of the sepals.

FIG. 8. Bud before opening the sepals.

FIG. 9. Flower petal, detached—outer surface.

FIG. 10. Flower petal, detached—inner surface.

FIG. 11. Open flower— plan view —reverse.

FIG. 12. Open flower— plan view —obverse

FIG. 13. Bare stem.

DETAILED BOTANICAL DESCRIPTION OF THE VARIETY

The following is a detailed description of the Floribunda Rose: *Rosa* hybrid 'Koramasti'.

The following observations, measurements, values and comparisons describe plants grown in glass houses in Klein Offenseth-Sparrieshoop, Germany. The age of the observed plants where 11 to 13 months after propagation by cuttings, and produced as flowering cut-rose plants.

Color references are made using The Royal Horticultural Society (London, England) Colour Chart, 1995, except where common terms of color are used. For a comparison, the nearest existing rose variety is 'TANkalcig', a rose variety described and illustrated in U.S. Plant Pat. No. 10,650. Chart 1 details several physical characteristics of 'Koramasti' and 'TANkalcig'.

CHART 1

| | 'Koremasti' | 'TANkalcig' |
|---|---|---|
| Petal color, Upper surface | Red Group 45A | Red Group 48A |
| Petal color, Reverse surface | Red Group 46A | Red Group 53A |
| Petal count | 30–35 | 30 |
| Parents | Unnamed Seedling | 'TANorelav' and 'KORlimit' |

Classification:

*Botanical.*—*Rosa hybrida.*

*Commercial.*—Floribunda.

Plant:

*Plant growth.*—Very vigorous. Grows strong upright to bushy, 70 cm high and 40 cm wide. Production time for floral stems is generally 6 to 8 weeks depending on average temperature, light level and cultural practices.

*Height.*—Plants which were pruned at height of 0.5 meter produce floral stems having a length of 45 cm.

Stem:

*Color.*—Young wood: Green Group 137A. Older wood: Green Group 137A.

*Thorns.*—Incidence: almost absent. Size: 5 mm. Color: reddish, Grey-red Group 181A. Shape: Deep concave, bending downward.

*Surface.*—Young wood: Smooth. Older wood: Smooth.

*Stem diameter.*—5–5.5 mm.

*Internode length.*—60–80 mm.

*Numbers of internodes.*—6–9.

Plant foliage: Leaves arranged alternately, compound with three to seven leaflets per leaf, generally symmetrical, abundant, and flat in aspect. Stipules at petiole base.

*Quantity of leaves.*—8 to 12 per lateral branch.

*Leaf size.*—Medium 150–160 mm(l). times. 100–110 mm(w).

*Petioles.*—Color: Green Group 137A. Margins: entire with almost no thorns. Length: 20 mm Diameter: about 1–1.5 mm.

*Stipules.*—Size: 10–12 mm. Surface: Smooth. Color: Green Group 144A. Margins: single, serrated.

*Rachis.*—Color: Green Group 144A. Margins: Margins with few prickles. Length: 20 to 25 m.

*Leaflets.*—Edge: Serrated. Serration: single. Shape: Ovate with rotundate base. Texture: Smooth (upper and lower side). Appearance: Shiny. Size: length: 55 to 60 mm. Width: 35 to 40 mm. Color: Young foliage: Upper surface: Green Group 137A. Lower surface: Green Group 137B. Color: Mature foliage: Upper surface: Green Group 137A. Lower surface: Green Group 137B.

Inflorescense:

*Blooming habit.*—Recurrent.

*Number of flowers.*—Generally 1 bud per flowering stem.

*Peduncle.*—Color: Yellow-Green Group 144B. Texture: Smooth. Length: 65–70 mm. Strength: strong.

*Receptacle.*—Surface: Smooth. Shape: Funnel-shaped. Size: h: 10–12 mm. w: 9–10 mm. Color: Yellow-Green Group 144B.

*Sepals.*—Quantity: 5. Shape: Narrowly Ovate w. acute tip. Texture: Smooth. Margin: nearly no appendages. Appearance: Dull. Color: Upper surface: Yellow-Green Group 143C. Reverse surface: Yellow-Green Group 144A.

*Buds.*—Size: 35–40 mm (h) 25–28 mm (w) upon opening. Shape: Pointed. Color: at ¼ opening, Red Group 46A.

*Flower.*—Duration. As a cutflower, flowers last app. 16 days. Fragrance. None. Size: 75–80 mm in diameter. Form: Shape of flower when viewed from the side. Upon opening: Convex. Open flower: Rounded. Color: Petals, upon opening. Upper surface: Red Group 46A. Reverse surface: Red Group 46A. Petals after opening: Upper surface: Red Group 45A. Reverse surface: Red Group 46A. Petals spots of 3 mm diameter. Color: Yellow Group 7A. General tonality: On Open flower: Third day: Red Group 45 A. Afterwards: Red Group 45 A.

Petals:

*Petal reflex.*—Outermost petals reflex backwards moderately at opening. Fully open all petals reflex backwards moderately.

*Texture.*—Smooth.

*Petal edge.*—Uniform.

*Petal count.*—Approximately 30–35 on the average per flower.

*Petal size.*—Length 45 mm With: 40 mm.

*Shape.*—Outer petals: Round. Inner petals: Round.

Reproductive organs:

*Stamen number.*—Approximately 55–65 on average per flower.

*Pollen.*—Color: White Group 155D Abundance: Average.

*Anthers.*—Size: 1–2 mm Color: White Group 155D. Shape: Oblong.

*Filaments.*—Size: 8–10 mm Color: Red-Purple Group 57 A.

*Pistils number.*—Approximately 50–60 an average per flower.

*Stigmas.*—Location: Superior in location to anthers Color: White Group 155D to Yellow Group 4D.

*Styles.*—Color: Red-Purple Group 57B. Length: 4 to 5 mm.

Development:

*Vegetation.*—Dense.

*Blooming.*—Abundant.

*Aptitude to bear fruit.*—Poor.

*Resistance to diseases.*—Above average resistance to Powdery Mildew and Botrytis under normal growing conditions in Klein Offenseth-Sparrieshoop, Germany. Hips/seeds have not been observed due to that the plant has never been grown to the stage of seed development, due to the fact, that the variety is developed for producing floral stems only.

Winter hardiness & Drought/heat tolerance: Due to the fact, that this variety is a cut rose plant, developed for producing floral stems only, the plant is not tested for winter hardiness or drought/heat tolerance.

It is claimed:

1. A new and distinct variety of rose plant of the Floribunda class, substantially as herein illustrated and described as a distinct and novel rose variety due to its abundant red colored flowers, attractive long lasting foliage, vigorous and upright growth, year round flowering under glasshouse conditions, suitability for production from softwood cuttings, and durable flowers and foliage which make the variety suitable for distribution in the floral industry.

* * * * *

KORAMASTI